US005759857A

United States Patent [19]

Goyal et al.

[11] Patent Number: 5,759,857
[45] Date of Patent: Jun. 2, 1998

[54] LEAK DETECTION USING CHEMICAL MARKERS

[75] Inventors: Shri K. Goyal, Naperville, Ill.; Terrence A. Renner, Katy, Tex.; Ashok K. Jhawar, Naperville, Ill.

[73] Assignee: Amoco Corporation, Chicago, Ill.

[21] Appl. No.: 721,594

[22] Filed: Sep. 26, 1996

[51] Int. Cl.$^6$ ..................................................... G01N 31/00
[52] U.S. Cl. ......................... 436/3; 44/328; 44/600; 44/903; 261/157; 261/158; 261/159; 250/301
[58] Field of Search ........................ 436/3; 44/328, 44/600, 903; 261/157, 158, 159; 250/301

[56] References Cited

U.S. PATENT DOCUMENTS

| | | | |
|---|---|---|---|
| 2,689,171 | 9/1954 | Hager et al. | 23/230 |
| 3,087,064 | 4/1963 | Curtice et al. | 250/106 |
| 3,522,008 | 7/1970 | Defabaugh et al. | 23/230 |
| 3,764,273 | 10/1973 | Turner et al. | 23/230 |
| 3,790,345 | 2/1974 | Mansfield et al. | 23/230 R |
| 4,209,302 | 6/1980 | Orelup | 44/59 |
| 4,328,700 | 5/1982 | Fries | 73/40.7 |
| 4,688,627 | 8/1987 | Jean-Luc et al. | 165/11.1 |
| 4,735,631 | 4/1988 | Orelup | 44/59 |
| 5,156,653 | 10/1992 | Friswell et al. | 44/328 |
| 5,205,840 | 4/1993 | Friswell et al. | 44/428 |
| 5,252,106 | 10/1993 | Hallisy | 44/328 |
| 5,304,800 | 4/1994 | Hoots et al. | 250/302 |
| 5,306,343 | 4/1994 | Richardson, III et al. | 106/668 |

OTHER PUBLICATIONS

"Detecting Leaks in Hydrotreater Feed/Effluent Heat Exchangers Using Gasoline Dyes," Mar. 1982, American Cyanamid Company, Chemical Products Division, Worldwide Catalyst Department, Wayne, New Jersey 07470.

*Primary Examiner*—Tom R. Scheiner
*Attorney, Agent, or Firm*—Richard A. Kretchmer; Frank J. Sroka

[57] ABSTRACT

Leakage in a heat exchanger between two liquids which are in indirect heat exchange relationship is detected by marking one of the two liquids with a colorless chemical marker and detecting it in the second liquid by extraction and conversion to a colored material. The heat exchanger liquids are preferably organic liquids which are immiscible with water. The marker is detected in a heat exchanger liquid by extraction of the marker followed by chemical conversion of the marker to a colored material that can be detected visually. Aminoalkylnaphthalenes are suitable markers which can be extracted by an acidic aqueous solution and converted to a colored material by reaction with a diazotized aromatic amine. Phenylazoalkylphenol derivatives are also suitable markers which can be extracted and simultaneously converted to a colored material with a detection reagent which is comprised of water and a water-soluble amine.

22 Claims, 1 Drawing Sheet

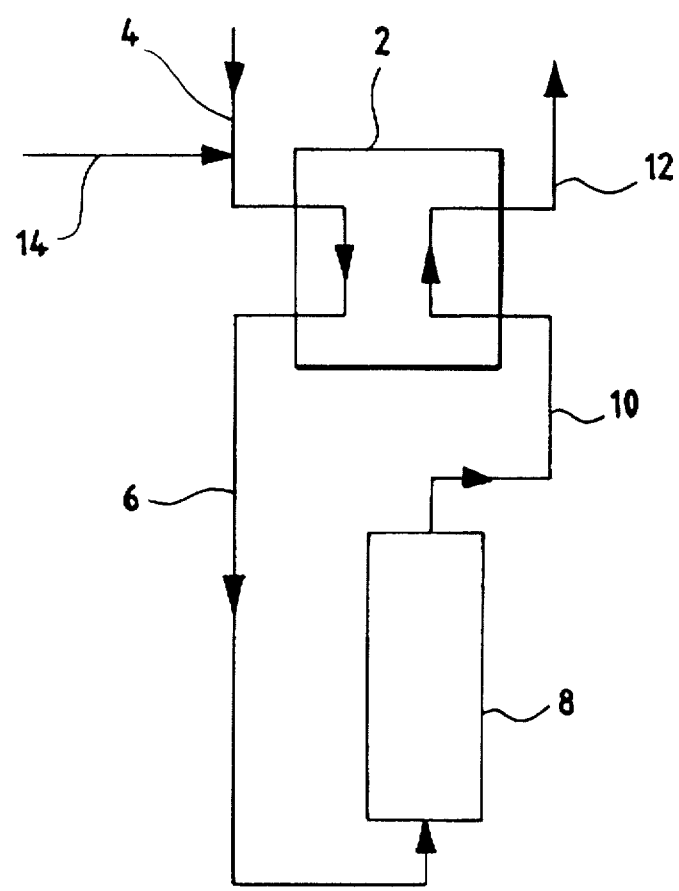

5,759,857

LEAK DETECTION USING CHEMICAL MARKERS

FIELD OF THE INVENTION

This invention relates to a method for the detection of leakage in a heat exchanger between two liquids which are in indirect heat exchange relationship. More particularly, the invention is an improved method for detecting the leak of a first liquid into a second liquid within a heat exchanger through the addition of a substantially colorless chemical marker to the first liquid and detecting the marker in the second liquid.

BACKGROUND OF THE INVENTION

Temperature control is required in many of the processes which are employed in chemical plants and oil refineries. In order to make such processes as efficient as possible, it is conventional to use one or more heat exchangers to indirectly transfer heat from one process stream to another. Typically, heat will be exchanged between a feed stream of raw material for the process and an effluent stream of product from the process. With processes that are operated at elevated temperatures, the heat exchanger will ordinarily be used to transfer heat from a product stream to a feed stream of raw material.

Unfortunately, leaks can and do occur in heat exchangers. If two liquids are placed in indirect heat exchange relationship in a heat exchanger, any breach in the heat exchanger walls that separate the liquids can result in the contamination of one liquid with the other. Although cross-contamination can take place, one liquid will usually be at a higher pressure than the other, and leakage will ordinarily involve a flow of liquid from the high to the low pressure side of the heat exchanger. Although it is not often observed in heat exchangers, it will also be appreciated that leakage can also involve a flow of liquid from the low pressure side to the high pressure side (an aspirator functions in this manner).

Chemical plant and oil refinery processes are usually carried out on a very large scale. Accordingly, a small amount of leakage can sometimes be tolerated in a heat exchanger which is associated with such a process. However, leakage above a certain amount, which will be dependent on the specific process and the type of contamination caused by the leakage, cannot be tolerated, and efforts to locate and repair it must be made expeditiously. As an example, most such processes are carried out for the purpose of changing the chemical and/or physical properties of a starting material. Therefore, any significant contamination of the product with starting material by way of a leak in a heat exchanger will usually be unacceptable.

Feed-product heat exchangers are commonly employed in petroleum refineries for processes, such as reforming, catalytic cracking, and hydrogenation, which employ elevated temperatures that can be in the range, for example, from about 100° to about 550° C. In many such processes, a low temperature feed stream and a high temperature product stream are passed through a heat exchanger wherein they are placed in heat exchange relationship but are physically segregated from each other. The feed stream then absorbs, through indirect heat exchange, part of the heat that is carried into the heat exchanger by the product stream. It is not uncommon in such a system to have a leak develop in the means separating the feed stream from the product stream in the heat exchanger. Any such leak will cause a feed and/or product loss or misdirection and product contamination if feed is leaked into the product.

To explore for a leak in a heat exchanger, or to verify the presence of a suspected leak, a marker is conventionally added to one of the two fluid streams that are in heat exchange relationship in the heat exchanger. The rapid appearance of any of the marker in the other fluid stream then serves to indicate the presence of a leak in the heat exchanger. In addition, the amount of the marker that is transferred from the one fluid to the other by way of the leak can be used to quantify the magnitude of the leak.

A variety of markers have been suggested for the detection of heat exchanger leaks. For example, U.S. Pat. No. 3,087,064 (Curtice et al.) discloses a method for detecting, and, if desired, measuring, leaks in feed-product heat exchangers by the addition of a radioactive tracer into the feed stream to the heat exchanger and monitoring the product stream from the heat exchanger for the appearance of any radiation. Unfortunately, sophisticated analytical procedures are necessary to detect the tracer, and special safety precautions must be used in handling the radioactive tracer. Further, the use of radioactive tracers is undesirable because of possible contamination of the product stream with radioactive material.

U.S. Pat. No. 4,688,627 (Jean-Luc et al.) is directed to a method for detecting leaks in heat exchangers which involves the addition of helium gas to one of the two fluids which are in indirect heat exchange relationship in a heat exchanger and monitoring the other fluid for the appearance of any of the helium. In practice this method is cumbersome and requires sophisticated detection apparatus such as a mass spectrometer.

U.S. Pat. No. 4,328,700 (Fries) discloses the use of sulfur hexafluoride gas as a marker for detecting leaks in heat exchangers. In this process, sulfur hexafluoride is added to one of the two fluids which are in heat exchange relationship in a heat exchanger while the other fluid is monitored for the appearance of any of the sulfur hexafluoride marker. Although sensitive equipment is available for the detection of the sulfur hexafluoride marker, this equipment is sophisticated and expensive.

American Cyanamid Company, in a brochure entitled "Detecting Leaks in Hydrotreater Feed/Effluent Heat Exchangers Using Gasoline Dyes," dated March, 1982, describes the use of a highly colored dye to detect leaks in heat exchanger wherein a feed stream to a chemical process is in indirect heat exchange relationship with a product stream from the process. The dye is injected into the feed and is selected so that the chemical reaction for which the feed stream is destined, such as hydrogenation, will transform the dye to a colorless material and thereby obviate simple mass transport through the chemical process as a source of the dye. Visual observation of the highly colored dye in the product stream from the heat exchanger is used as an indication of a leak between the feed and product streams in the heat exchanger. Unfortunately, if a leak exists in the heat exchanger, this approach will result in a colored product which may be undesirable or unacceptable.

U.S. Pat. No. 4,209,302 (Orelup) discloses a group of substantially colorless markers for use in identifying petroleum fuels, which can be detected in a marked fuel by: (1) extraction of the marker from the fuel with an acidic aqueous solution, and (2) treatment of the aqueous extract with diazotized 2-chloro-4-nitroaniline to produce a characteristic coloration. The markers are α-naphthylamine derivatives and β-naphthylamine derivatives; and suitable fuels include materials such as gasolines, diesel oils, heating or fuel oils, kerosenes, jet fuels, and naphthas. This reference does not, however, either teach or suggest that such a marker or analytical procedure could be used to identify leakage in a heat exchanger.

U.S. Pat. No. 5,156,653 (Friswell et al.) discloses a group of substantially colorless phenylazophenol derivatives which are useful for tagging liquid petroleum products. These markers are detected by extraction with a reagent which is comprised of water and a water-soluble amine. The reagent system extracts the marker from the liquid petroleum product and also reacts with the marker to produce a color that can be detected visually. However, this reference also fails to teach or suggest that such a marker or analytical procedure could be used to identify leakage in a heat exchanger.

SUMMARY OF THE INVENTION

Conventional methods for detecting leaks in heat exchangers are not fully satisfactory. Many of the prior art methods require complex and expensive instrumentation together with highly skilled personnel for its operation. Often this instrumentation must be operated in a laboratory which is distant from the heat exchanger, thereby introducing a significant time delay between sampling and detection. Other prior art methods can result in the contamination of a product stream from the heat exchanger with either a radioactive or highly colored material. In particular, there is a need for a simple and convenient leak detection procedure which does not cause an objectionable contamination of the liquids flowing through the heat exchanger and can be carried out in the field by relatively unskilled personnel. We have found that an improved leak detection procedure of this type is possible through the use of very small amounts of substantially colorless chemical markers which can be chemically converted to a colored material.

One embodiment of the invention is a method for detecting the leak of a first liquid into a second liquid within a heat exchanger, wherein said liquids are in indirect heat exchange relationship within the heat exchanger, which comprises: (a) adding a substantially colorless chemical marker to the first liquid prior to its entry into the heat exchanger; (b) withdrawing a sample of the second liquid subsequent to its exit from the heat exchanger; and (c) analyzing said sample for the presence of the chemical marker by extracting a portion of any marker from the sample and chemically converting the extracted marker to a colored material.

Another embodiment of the invention is a method for detecting the leak of a first liquid into a second liquid within a heat exchanger, wherein said liquids are in indirect heat exchange relationship within the heat exchanger, which comprises: (a) adding a substantially colorless chemical marker to the first liquid prior to its entry into the heat exchanger; and (b) monitoring the second liquid for the appearance of any chemical marker by periodically withdrawing samples of said second liquid subsequent to its exit from the heat exchanger and analyzing each sample for the presence of the chemical marker by extracting a portion of any marker from the sample and chemically converting the extracted marker to a colored material.

An object of the invention is to provide a method for the detection of heat exchanger leaks through the use of a chemical marker which will not result in an undesirable contamination of any of the fluids flowing through the heat exchanger.

An object of the invention is to provide a method for the detection of heat exchanger leaks which does not require sophisticated or expensive analytical equipment.

An object of the invention is to provide a method for the detection of heat exchanger leaks which can be carried out by relatively unskilled personnel.

An object of the invention is to provide a method for the detection of heat exchanger leaks which can be carried out quickly at the site of the heat exchanger without any need to transport samples to a remote laboratory for analysis.

Another object of the invention is to provide a method for the detection of heat exchanger leaks which can be carried out at high temperatures.

A further object of the invention is to provide a method for the detection of heat exchanger leaks that can be used when the fluids passing through the heat exchanger are highly colored.

BRIEF DESCRIPTION OF THE DRAWINGS

The drawing is a schematic representation of a chemical process reactor in combination with a feed-product heat exchanger which illustrates the use of the invention to detect leakage in the heat exchanger.

DETAILED DESCRIPTION OF THE INVENTION

The present invention is directed to a method for detecting heat exchanger leaks which employs a thermally stable and substantially colorless chemical marker which is easily detected and will impart no undesirable characteristics to any of the fluids flowing through the heat exchanger. The chemical marker is added to one of two liquids which are in heat exchange relationship in the heat exchanger, and the appearance of the marker in the other liquid together with the precise timing of this appearance serves to indicate the presence of a leak. The detection of the chemical marker in a heat exchanger fluid is accomplished by extracting the marker from the heat exchanger fluid with an immiscible extracting liquid and chemically converting the extracted marker to a colored material.

The invention can be used to detect leaks in any conventional heat exchanger wherein two liquids are in indirect heat exchange relationship. Desirably, both of these liquids will be comprised of organic compounds which are substantially immiscible with water. In a preferred embodiment, at least one of the liquids will be comprised of hydrocarbons. In a highly preferred embodiment, both of the liquids will be comprised of hydrocarbons. It will be appreciated, of course, that one or both of these liquids can be either a pure chemical compound or a mixture of chemical compounds.

The heat exchanger liquids can be either colorless or highly colored. In a heat exchanger wherein two liquids are in indirect heat exchange relationship, leakage of a colorless first liquid into a highly colored second liquid is easily detected. Alternatively, both the first and second liquid can be either colorless or highly colored. As an illustration, leakage can be easily detected in a heat exchanger which is associated with a pipe still for the distillation crude oil wherein crude oil and vacuum resid are placed in indirect heat exchange relationship in the heat exchanger. Both the crude oil and the vacuum resid will be very dark colored liquids.

Many organic liquids which are passed through heat exchangers in industrial processes are highly colored and are typically black in appearance. Examples of such liquids which can be used as heat exchanger liquids in this invention include crude petroleum, shale oil, coal liquids, products from coal liquefaction, tar sands bitumen. Additional examples include various fractions of such materials such as gas oils, atmospheric resid and vacuum resid from the distillation of petroleum; various refinery process streams such as decanted oil, heavy cycle oil and light cycle oil from a fluidized catalytic cracking unit, gas oil from a coker, and hydrotreated gas oil; black liquor resulting from the soda or sulfate paper-making process; and quench oil used in pyrolytic processes for the production of olefins.

The chemical markers which are suitable for use in the practice of this invention are substantially colorless whose presence can be detected visually by extracting the marker from the liquid in which it is contained and chemically converting the extracted marker to a colored material. The marker is extracted from the marked liquid with an extraction liquid which is substantially immiscible with the marked liquid. Desirably, the extraction liquid will be aqueous in character and will comprise at least about 10% by weight of water and, preferably, at least about 50% by weight of water. If the chemical marker is either acidic or basic, the pH of the extraction liquid can be adjusted to maximize the extraction of the marker. Desirably, a major portion of the chemical marker will be extracted from the marked liquid by the extraction liquid and, preferably, substantially all of the chemical marker will be extracted.

Extraction of the chemical marker provides a simple and convenient method to concentrate small amounts of the marker and to remove it from any highly colored materials that might also be present in the marked liquid. Preferred chemical markers yield an intense coloration upon conversion to the colored material. Concentration of the chemical marker by extraction in combination with conversion to an intensely colored material affords a rapid and simple method for detection of trace amounts of the marker.

If the liquid which is to be tested for the presence of the chemical marker is viscous, extraction of the marker can be facilitated by dilution of the viscous liquid with a low viscosity diluent. Such viscous liquids will typically have a viscosity which is in excess of about 30 centipoises at 20° C., and the volume of the diluent will typically be equal to or less than that of the sample of viscous liquid that is to be analyzed. Examples of such viscous liquids include, but are not limited to, atmospheric resid, vacuum resid, and decanted oil from a fluidized catalytic cracking process; and suitable low viscosity diluents for these examples would include hexane, benzene, toluene, xylene, naphtha, gasoline, and kerosene.

A preferred chemical marker for use in the practice of this invention comprises at least one material which is selected from the group consisting of compounds of the formula I, II, III, IV and V:

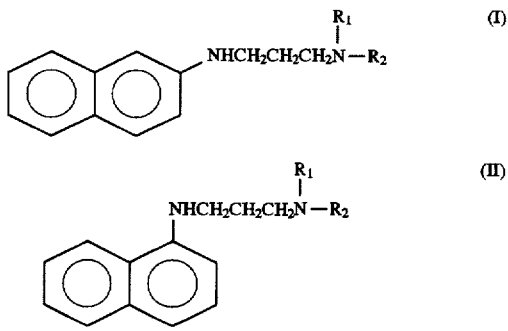

where $R_1$ and $R_2$ are independently selected from the group consisting of hydrogen and alkyl groups of from one to twenty carbon atoms,

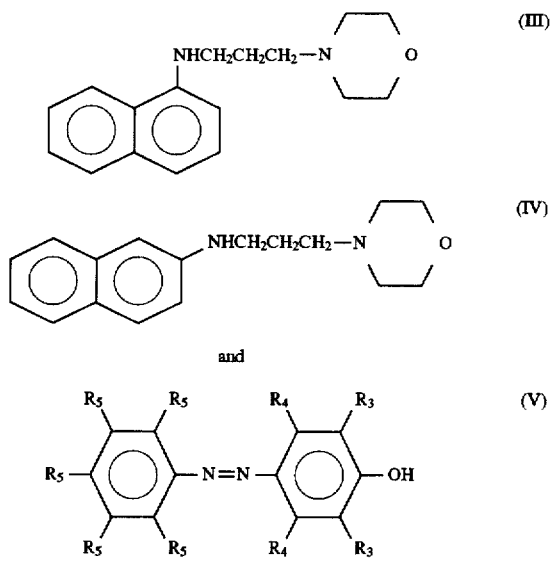

where each $R_3$ and $R_4$ is independently selected from the group consisting of hydrogen and alkyl groups of from one to seven carbon atoms, provided that at least one $R_3$ is an alkyl group of from three to seven carbon atoms, and each $R_5$ is independently selected from the group consisting of —H, —NO$_2$, —Cl, —Br, —F, —CN, and —CH$_3$, provided that at least one $R_5$ is selected from —NO$_2$, —Cl, —Br, —F, and —CN.

Compounds of the formula I, II, III, and IV are referred to herein as aminoalkylnaphthalenes. The use of these compounds as markers for petroleum fuels is disclosed in U.S. Pat. No. 4,209,302 (Orelup). This patent is hereby incorporated by reference. Mixtures of such aminoalkylnaphthalenes are commercially available from Morton International, Inc., under the trade name Mortrace MP. The preparation of compounds of the formula I and III is described in the Orelup patent.

Compounds of the formula V are referred to herein as phenylazoalkylphenol derivatives. The use of such compounds to mark liquid petroleum products is disclosed in U.S. Pat. No. 5,156,653 (Friswell et al.). This patent is hereby incorporated by reference. Mixtures of such phenylazoalkylphenols are commercially available from Morton International, Inc., under the trade name Mortrace SB. The preparation of compounds of the formula V is described in the Friswell et al. patent.

When aminoalkylnaphthalenes are used as chemical markers in the practice of this invention, the marker is detected by extracting the marked hydrocarbon liquid with an acidic aqueous solution and thereby removing the marker from the hydrocarbon liquid and transferring it to the aqueous phase. The resulting aqueous extract is then treated with a diazonium salt which is prepared by diazotization of an aromatic amine. The presence of a marker is indicated by the formation of a highly colored azo compound that results from the coupling of the diazotized aromatic amine with the aminoalkylnaphthalene marker. The colored azo compound is chemically related to and can be considered a member of the class of compounds known as azo dyes. Substantially any aromatic amine can be diazotized and used to detect the aminoalkylnaphthalene markers of this invention. Suitable aromatic amines include, but are not limited to, 2-chloro-4-nitroaniline, 2-chloroaniline, 4-chloroaniline, and 2-nitroaniline. However, diazotized 2-chloro-4-nitroaniline is highly preferred and yields a characteristic pink coloration when combined with compounds of the formula I, II, III, and IV.

The acidic aqueous solution which is used to extract the aminoalkylnaphthalene markers of this invention can be an aqueous solution of any strong acid. Such solutions include, but are not limited to aqueous solutions of acetic acid, propionic acid, hydrochloric acid, sulfuric acid, and methanesulfonic acid. However, an aqueous solution of methanesulfonic acid or hydrochloric acid is preferred. A satisfactory methanesulfonic acid solution will contain from about 0.3% to about 3% by weight of methanesulfonic acid, and a satisfactory hydrochloric acid solution will contain from about 0.1% to about 3% by weight of HCl in water. However, it will be appreciated that the precise acid and its concentration can be varied widely.

The diazotized 2-chloro-4-nitroaniline which is preferred for use in detecting the aminoalkylnaphthalene markers of this invention can be prepared by diazotizing 2-chloro-4-nitroaniline in a non-aqueous medium such as glacial acetic acid. The resulting solution is very stable and can be stored at room temperature for several months.

The aminoalkylnaphthalene markers of this invention, as pure compounds, are sufficiently soluble in hydrocarbon liquids for convenient use in the practice of this invention. However, for even greater convenience, in handling, storage and metering into liquids which are to be marked, the aminoalkylnaphthalene markers can be converted into concentrated solutions by admixture with fatty acids and conventional hydrocarbon solvents. For example, a typical concentrated solution could consist of 34% by weight of a compound of formula II, 39% by weight of oleic acid, and 27% by weight of xylene. The specific fatty acids and solvents, and their proportions, may be varied as desired.

When phenylazoalkylphenol derivatives are used as chemical markers in the practile of this invention, the marker is detected by extracting the marked hydrocarbon liquid with a detection reagent which is comprised of water and a water-soluble amine. This detection reagent will typically comprise from about 10 to 60 volume percent water and from about 10 to 60 volume percent of a water-soluble amine. Preferably, the reagent will also contain up to about 60 volume percent of a cosolvent which is miscible with water and substantially immiscible in the marked hydrocarbon liquid. Although the cosolvent is not necessary, it can have an advantageous effect on the shade, intensity and stability of the color that is produced when the detection reagent interacts with the marker. The color produced by the detection reagent will be a function of the precise character of the $R_3$, $R_4$ and $R_5$ substituents in the phenylazoalkylphenol derivatives of formula V.

Suitable water-soluble amines for use in the detection reagent for the phenylazoalkylphenol derivative markers include water-soluble alklyl amines, such as butylamine, water-soluble alkoxy amines, such as 3-methoxypropylamine, 4-(3-aminopropyl)morpholine, and methoxy ethoxy propylamine and mixtures thereof.

Suitable cosolvents for use in the detection reagent for the phenylazoalkylphenol derivative markers include alcohols, such as ethyl alcohol; glycols, such as ethylene glycol, di(ethylene glycol), proplylene glycol, di(propylene glycol), poly(ethylene glycol), poly(propylene glycol); glycerin; esters such as methyl lactate, ethyl lactate and butyl lactate; sulfolane; dimethyl sulfoxide and N,N-dimethylformamide. Preferred cosolvents are the more oxygenated materials, such as glycerin, di(ethylene glycol) and poly(ethylene glycol) having an average molecular weight of about 300 and mixtures thereof.

The phenylazoalkylphenol derivatives of formula V are typically solids. Although they can be used as pure compounds in the practice of this invention, it is generally more convenient to use them as a concentrated solution in a suitable solvent. Such solvents will, of course, be miscible with the hydrocarbon liquids which are undergoing heat transfer in the heat exchanger that is to be analyzed for possible leakage. Xylene is a particularly satisfactory solvent.

Compounds of the formula I, II, III, IV and V are detectable by extraction and conversion to a colored material at a concentration level as low as about 0.25 ppm to 0.5 ppm by weight. Accordingly, it is possible to detect leaks in a heat exchanger through the use of very low concentrations of chemical marker. For example, if the leakage in the heat exchanger is such that one of the two liquids that pass through the heat exchanger is contaminated at a 1% level by leakage, that leakage can be detected by using as little as 50 ppm by weight of marker in the liquid that is causing the contamination. The contaminated liquid will then contain 0.5 ppm by weight of the chemical marker. It will be appreciated, of course, that the actual amount of the chemical marker used will be determined by the precise chemical marker selected, the desired intensity of color produced upon extraction and color development, and the magnitude of the heat exchanger leak.

The extraction of the chemical marker in the practice of this invention serves to remove it from any highly colored materials that might also be present in the marked liquid. In addition, the extraction can be used to concentrate the marker by extracting a large volume of marked liquid with a much smaller volume of the liquid which is used for the extraction. Typically, the volume ratio of extraction liquid to marked liquid will be from about 1:1 to about 1:20.

With reference to the drawing, a cool hydrocarbon feedstock flows into feed-product heat exchanger 2 through line 4. The feedstock absorbs heat within heat exchanger 2 and is then discharged through line 6 and passes into chemical process reactor 8 where the feedstock undergoes chemical transformation at a high temperature. Hot product is discharged from reactor 8 and passes through line 10 to heat exchanger 2 where heat is transferred to the heat exchanger. Finally, cool product is discharged from heat exchanger 2 through line 12. Heat exchanger 2 effects an indirect transfer of heat from the hot product of reactor 8 to the cool feedstock before it is introduced into reactor 8, thereby enhancing the thermal efficiency of the process.

A heat exchanger transfers heat indirectly by means of thermal conduction through the walls that separate the hot liquid from the cool liquid. Unfortunately, leaks can develop in these walls. Any such leak can result in the contamination of one liquid with the other. In one embodiment of the present invention, the feedstock is at a higher pressure in the heat exchanger than the product, and the chemical marker is added to the feedstock through line 14. The resulting mixture is then passed through heat exchanger 2 in which a leak is suspected. The presence or absence of a leak in heat exchanger 2 is determined by sampling the product from line 12, extracting any marker from the sample and converting the extracted marker to a colored material.

The amount of chemical marker to be added through line 14 and the period of time over which it is added are determined by: (a) the known volume and flow rate of the feedstock and product streams that pass through heat exchanger 2; and (b) the size of the leak. For chemical markers of the formula I, II, III, IV and V, a concentration of marker as low as about 0.5 ppm by weight can be detected by extraction from a sample of the product stream and conversion to a colored material. Accordingly, the concentration of marker in the feedstock stream will not, ordinarily, need to exceed about 50 ppm to about 100 ppm by weight. However, these concentrations of marker will not appreciably color either the feedstock stream or the product stream. In addition, these concentrations of marker are sufficiently small that they will not ordinarily represent an undesirable contamination.

After the addition of the chemical marker though line 14, a period of time will be required to permit: (i) the marked feedstock to flow into heat exchanger 2; (ii) the leakage of marked feedstock into the product stream within heat exchanger 2; and (iii) the flow of product which is contaminated with marked feedstock out of heat exchanger 2. Accordingly, it will frequently be desirable to monitor the product stream effluent from heat exchanger 2 for the presence of the chemical marker over a period of time beginning with the addition of marker to the feedstock input to heat exchanger 2. In the event of a leak in the heat exchanger, this procedure comprises a monitoring of the rise and fall of the chemical marker concentration as it is leaked into the product stream. Alternatively, the product stream effluent from the heat exchanger can be sampled only once if it is known, based on flow rates and the volumes of the heat exchanger and associated piping, when any leakage of the chemical marker will appear in the product stream at the sampling point. The appearance of the marker in the product stream effluent at a point in time which is possible only as a consequence of a leak in the heat exchanger serves to indicate the existence of such a leak, and the absence of any marker in the product stream at such time indicates the absence of a leak.

In the practice of this invention, it must be remembered that the chemical markers can be very inert with respect to conditions which will cause the chemical transformation or decomposition of many other types of organic chemicals. More specifically, some or substantially all of the chemical marker which is added to the feedstock stream through line 14 can pass unchanged through chemical process reactor 8. For example, we have found that aminoalkylnaphthalene chemical markers of this invention can be passed through a fluidized catalytic cracking unit without change. Such a marker was used to test for leakage in a heat exchanger wherein atmospheric resid was in heat exchange relationship with decanted oil. It was found that the marker which was added to the atmospheric resid feedstock survived high temperature exposure to cracking catalyst in the associated fluidized catalytic cracking unit. In addition, the marker was easily detectable in the resid and decanted oil, which are dark and viscous hydrocarbon mixtures, at concentrations in the range from 1 to 3 ppm by weight.

If desired, the magnitude of a leak in a heat exchanger can be measured by means of the subject invention. Conversion of the chemical marker of this invention to a colored material can be used as the basis for a quantitative determination of chemical marker concentration. The marker concentration can be determined by extraction of the marker, chemical conversion of the marker to a colored material, and measurement of the color intensity. Precise measurement of the color intensity can be carried out using a spectrophotometer or, alternatively, can be carried out visually by comparison with standards which are prepared using known concentrations of the marker. Accordingly, the magnitude of a leak can be calculated based on the following information: (i) the concentration of chemical marker in the marked heat exchanger liquid which will be known based on the amount of marker added; (ii) the concentration of chemical marker leaked into the other heat exchanger liquid which can be measured in the above described manner; and (iii) the flow rates of the two liquids through the heat exchanger.

EXAMPLE 1

In order to test for leakage within a feed-product heat exchanger which is associated with a refinery hydrotreating unit, a mixture of aminoalkylnaphthalenes is added as a chemical marker to the hydrocarbon feedstock stream to the heat exchanger. The chemical marker is obtained from Morton International, Inc. under the trade name Mortrace MP as a solution which contains 40% by weight of the aminoalkylnaphthalenes. On the basis of the volumetric flow rates of the liquids passed through the heat exchanger, it is calculated that approximately 4 kilograms of Mortrace MP will mark this process stream at a chemical marker concentration of about 100 ppm by weight when added to the feedstock stream at a uniform rate over a period of 5 minutes. This amount of Mortrace MP is uniformly added over a 5 minute period to the feedstock input stream through a valved tap immediately in front of the heat exchanger. The marked feedstock has a residence time in the heat exchanger of approximately 15 seconds. Approximately 2 minutes after starting the addition of the marker to the feedstock input stream to the heat exchanger, a 20 milliliter sample of the effluent stream of hydrocarbon product from the heat exchanger is removed through a valved tap in the effluent product line and placed in a glass separatory funnel. To this sample is added 2 milliliters of an aqueous solution which contains 20% by weight of ammonium chloride and 20% by weight of acetic acid. The resulting mixture is then vigorously mixed by manual shaking. After shaking for one minute, the separatory funnel is opened and 0.25 milliliter of an acetic acid solution of diazotized 2-chloro-4-nitroaniline (containing acetic acid, sulfuric acid and diazotized 2-chloro-4-nitroaniline in a weight ratio of 85:10:10:) is added to the mixture. The resulting mixture is briefly shaken and then allowed to stand undisturbed for a brief period of time until the mixture separates into a lower aqueous layer and an upper hydrocarbon layer. The lower aqueous layer is observed to have assumed a bright red color which is characteristic of the developed chemical marker. This color formation demonstrates the presence of a leak in the heat exchanger which permits some of the marker to migrate from the feedstock stream into the product stream.

EXAMPLE 2

The compatibility of the aminoalkylnaphthalene chemical markers of this invention with a variety of conventional refinery process streams was evaluated by mixing a variety of such liquids with such a marker, extracting the marker with an aqueous liquid, and chemically converting the extracted marker to a colored material. High viscosity naphtha, coker plant distillate, vacuum gas oil and high sulfur resid were tested in this manner. To each of these liquids was added a sufficient amount of a mixture of aminoalkylnaphthalenes (Mortrace MP, obtained from Morton International, Inc.) to give marker concentration of about 5 ppm by weight. In each case, a 20 milliliter sample of the marked liquid was mixed with 2 milliliters of aqueous extraction liquid (MP Extractant A20, obtained from Morton International, Inc.) and 0.25 milliliter of a solution of diazotized aromatic amine (MP Color Developing Reagent, obtained from Morton International, Inc.). In each case, a bright red color appeared in the lower aqueous layer after the mixture was vigorously shaken for approximately one minute and then allowed to separate into an upper hydrocarbon layer and a lower aqueous layer.

We claim:

1. A method for detecting the leak of a first liquid into a second liquid within a heat exchanger, wherein said liquids are in indirect heat exchange relationship within the heat exchanger, which comprises:

(a) carrying out a process wherein said first and second liquids are process streams which are substantially organic in character and are selected from the group consisting of feedstock and products of said process;

(b) adding a substantially colorless chemical marker to the first liquid prior to its entry into the heat exchanger;

(c) withdrawing a sample of the second liquid subsequent to its exit from the heat exchanger; and (d) analyzing said sample for the presence of the chemical marker by extracting a portion of any marker from the sample and chemically converting the extracted marker to a colored material.

2. The method of claim 1 wherein said first liquid is at a higher pressure than said second liquid.

3. The method of claim 1 wherein a major portion of the chemical marker is extracted from the sample.

4. The method of claim 1 wherein the chemical marker is extracted with an extraction liquid which is substantially immiscible with said second liquid.

5. The method of claim 4 wherein said first and second liquids are substantially immiscible with water.

6. The method of claim 5 wherein said extraction liquid is an aqueous liquid.

7. The method of claim 6 wherein said extraction liquid comprises at least about 50% by weight of water.

8. The method of claim 5 wherein said first liquid is substantially hydrocarbon in character.

9. The method of claim 8 wherein the chemical marker is dissolved in a solvent which is miscible with said first liquid before addition to said first liquid.

10. The method of claim 5 wherein said second liquid is substantially hydrocarbon in character.

11. The method of claim 10 wherein said second liquid is dark in color.

12. The method of claim 11 wherein said second liquid has a viscosity in excess of about 30 centipoises at 20° C.

13. The method of claim 12 wherein the viscosity of the second liquid is reduced by addition of a low viscosity solvent prior to extraction of the chemical marker.

14. The method of claim 8 wherein the chemical marker comprises at least one material which is selected from the group consisting of compounds of the formula I, II, III, IV and V:

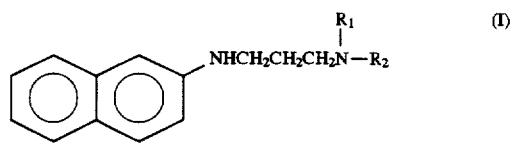

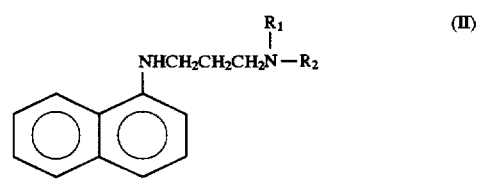

where $R_1$ and $R_2$ are independently selected from the group consisting of hydrogen and alkyl groups of from one to twenty carbon atoms,

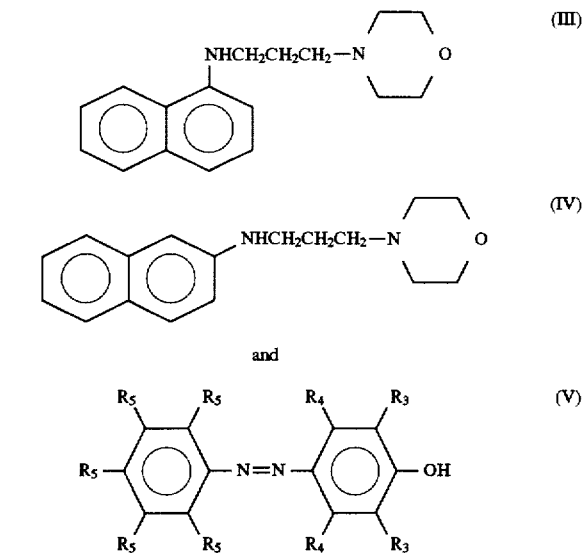

where each $R_3$ and $R_4$ is independently selected from the group consisting of hydrogen and alkyl groups of from one to seven carbon atoms, provided that at least one $R_3$ is an alkyl group of from three to seven carbon atoms, and each $R_5$ is independently selected from the group consisting of —H, —$NO_2$, —Cl, —Br, —F, —CN, and —$CH_3$, provided that at least one $R_5$ is selected from —$NO_2$, —Cl, —Br, —F, and —CN.

15. The method of claim 14 wherein the chemical marker is selected from the group of compounds having formulas I, II, III and IV, and wherein the chemical marker is converted to a colored material by treatment with a diazotized aromatic amine.

16. The method of claim 15 wherein said diazotized aromatic amine is selected from the group consisting of diazotized 2-chloro-4-nitroaniline, 2-chloroaniline, 4-chloroaniline, and 2-nitroaniline.

17. The method of claim 14 wherein the chemical marker has formula V, and wherein the chemical marker is converted to a colored material by treatment with a water-soluble amine.

18. The method of claim 17 wherein the extraction liquid comprises an aqueous solution of said water-soluble amine.

19. The method of claim 18 wherein the extraction liquid additionally comprises an oxygenated cosolvent which is selected from the group consisting of alcohols, glycols, glycerin, esters, sulfolane, dimethyl sulfoxide, N,N-dimethylformamide and mixtures thereof.

20. A method for detecting the leak of a first liquid into a second liquid within a heat exchanger, wherein said liquids are in indirect heat exchange relationship within the heat exchanger, which comprises:

(a) carrying out a process wherein said first and second liquids are process streams which are substantially organic in character and are selected from the group consisting of feedstock and products of said process;

(b) adding a substantially colorless chemical marker to the first liquid prior to its entry into the heat exchanger; and (c) monitoring the second liquid for the appearance of any chemical marker by periodically withdrawing samples of said second liquid subsequent to its exit from the heat exchanger and analyzing each sample for the presence of the chemical marker by extracting a portion of any marker from the sample and chemically converting the extracted marker to a colored material.

21. The method of claim 1 wherein said first liquid is a feedstock for said process and said second liquid is a product from said process.

22. The method of claim 1 wherein said first liquid is a product from said process and said second liquid is a feedstock for said process.

* * * * *

UNITED STATES PATENT AND TRADEMARK OFFICE
CERTIFICATE OF CORRECTION

PATENT NO.: 5,759,857
DATED: June 2, 1998
INVENTOR(S): Shri K. Goyal, Terrence A. Renner, Ashok K. Jhawar It is certified that error appears in the above-identified patent and that said Letters Patent is hereby corrected as shown below:

| Col. | Line | |
|---|---|---|
| 7 | 33 | reads "in the practile of this invention" should read --in the practice of this invention-- |
| 7 | 58 | reads "proplylene glycol" should read --propylene glycol-- |

Signed and Sealed this

First Day of December, 1998

Attest:

BRUCE LEHMAN

Attesting Officer     Commissioner of Patents and Trademarks